US005097082A

United States Patent [19]

Anton

[11] Patent Number: 5,097,082
[45] Date of Patent: Mar. 17, 1992

[54] PRODUCTION OF SATURATED HALOHYDROCARBONS

[75] Inventor: Douglas R. Anton, Claymont, Del.

[73] Assignee: E. I. Du Pont de Nemours and Company, Wilmington, Del.

[21] Appl. No.: 607,754

[22] Filed: Oct. 31, 1990

Related U.S. Application Data

[63] Continuation-in-part of Ser. No. 533,333, Jun. 5, 1990, abandoned.

[51] Int. Cl.$^5$ .................. C07C 17/00; C07C 19/08
[52] U.S. Cl. ........................ 870/175; 570/176; 570/181
[58] Field of Search .............. 570/170, 175, 176, 181

[56] References Cited

U.S. PATENT DOCUMENTS 2,844,636 7/1958 Haszletine ........................... 260/653
3,453,202 7/1969 Friedman et al. ................... 208/40

FOREIGN PATENT DOCUMENTS 0324478 7/1989 European Pat. Off. .
1578933 11/1980 United Kingdom .

OTHER PUBLICATIONS

R. N. Haszeldine et al., J. Chem. Soc., pp. 3380-3888 (1955), Fluoro-olefins, Part III.
H. Kubota, "Studies on Kinetics of the Gas-Phase Addition Reaction of HI to Butadiene I," Rev. Phys. Chem. Jap., 37, pp. 25-42 (1967).
V. F. Snegirev et al., "Catalytic and Hydride Reduction of Hexafluoropropylene Dimers," Izv. Akad. Nack. SSSR (1983) (1984 Plenum Translation).
Li Jisen et al., "Palladium-Catalyzed Hydrogenation of Hexafluoropropylene Dimers and Tetrafluoroolefin Tetramers", Shanghai Inst. Org. Chem., Youji Huaxue, vol. 1, pp. 40–42, 24, (1984).
R. D. Chambers et al., "Polyfluoroheterocyclic Compounds, Part XVIII, Reactions of Heptafluoro-quinoline and -isoquinoline and Pentafluoropyridine with Hydrogen Halides," J. Chem. Soc., pp. 61-67 (1971).
A. N. Bose et al., "Kinetics of the Reaction of HI with Propylene," Jour. Chem. Phys., vol. 37, pp. 1081-1084 (1962).
S. L. Shapiro et al., "Monomer Synthesis Triazines, A Novel Method for the Reduction of Halomethyl Groups in the Triazine Series," J. Am. Chem. Soc., vol. 76, pp. 97-100 (1954).
A. H. Blatt et al., "The Reduction of Picrylchloride to 1,3,5-Trinitrobenzene," J. Am. Chem. Soc., vol. 74, pp. 6273-6274 (1952).

Primary Examiner—Alan Siegel

[57] ABSTRACT

A process is disclosed for producing saturated halohydrocarbons containing fluorine which comprises the step of reacting certain saturated or olefinic compounds at an elevated temperature with hydrogen in the presence of at least one material selected from the group consisting of iodine and hydrogen iodide, or with hydrogen iodide. Also disclosed is a process for producing certain chloromethanes which comprises the step of reacting $CCl_4$ at an elevated temperature with hydrogen in the presence of iodine and/or HI, or with hydrogen iodide; and a process for producing $CF_3CCl=CHCF_3$ which comprises the step of reacting $CF_3CCl=CClCF_3$ at an elevated temperature with hydrogen in the presence of iodine and/or HI, or with hydrogen iodide.

19 Claims, No Drawings

PRODUCTION OF SATURATED HALOHYDROCARBONS

CROSS-REFERENCE TO RELATED APPLICATION

This application is a continuation-in-part of U.S. Pat. application Ser. No. 07/533,333 filed June 5, 1990 now abandoned.

FIELD OF THE INVENTION

This invention relates to the production of halogen-substituted hydrocarbons, and more particularly to the production of saturated halohydrocarbons.

BACKGROUND OF THE INVENTION

The production of saturated halohydrocarbons containing fluorine has recently been the subject of renewed interest as the products are identified as environmentally desirable compounds for use as solvents, blowing agents and refrigerants. The compounds have been produced using certain well-known catalytic processes for hydrogenolysis and/or hydrogenation of saturated or unsaturated compounds containing chlorine and fluorine.

Numerous catalysts for the hydrogenolysis or hydrogenation of halocarbons, including supported precious metal catalysts, are known. For example, British Pat. Specification No. 1,578,933 discloses a process for the manufacture of $CF_3CH_2F$ or $CHF_2CHF_2$ by the hydrogenolysis of an appropriate haloethane over a hydrogenation catalyst. Palladium supported on carbon or alumina are specifically exemplified. In a typical example, $CF_3CCl_2F$ is converted to a mixture of $CF_3CHClF$, $CF_3CH_2F$, and $CF_3CH_3$. European Pat. Publication No. 0324478 discloses a process for the preparation of 1,2-difluoroethane and 1,1,2-trifluoroethane which comprises reacting 1,1,2-dichloro-difluoroethylene or chlorotrifluoroethylene, respectively, with hydrogen in the gas phase in the presence of a hydrogenation catalyst comprising a transition metal; with palladium being preferred.

Supported metal catalysts such as palladium on carbon can exhibit poor selectivity. For example, in European Publication No. 0324478 it is seen that not only is hydrogen added to the olefinic bond, but chlorine atoms of the olefin are also replaced with hydrogen. It is clear that there is a need for more selective catalysts which allow control of reactions in order to produce not only fluorohydrocarbons (i.e., compounds containing only carbon, fluorine and hydrogen atoms) but also fluorohalohydrocarbons containing atoms of a halogen such as chlorine.

Precious metal catalysts such as palladium are expensive and can deactivate during the course of catalyzed reactions. Replacement and/or regeneration of such catalysts can thus add to the cost of the catalyzed reaction.

Iodine or hydrogen iodide have been used in conjunction with the reaction of certain perfluoro compounds. For example, U.S. Pat. No. 2,844,636 discloses a process for the manufacture of 1,1,2,3,4,4-hexafluorobutane by reacting perfluorocyclobutene with hydrogen, using elemental iodine as the catalyst. In this process not only is there hydrogen addition at the double bond, but also cleavage and hydrogenation at the $-CF_2-CF_2-$ single bond to give the substituted normal butane. R. D. Chambers et al., J. Chem. Soc.(C), 1971, 61-67; disclose the reaction of perfluoroquinoline with an excess of hydrogen iodide to form 3,5,6,7,8-pentafluoroquinoline.

SUMMARY OF THE INVENTION

A process is provided in accordance with this invention for producing saturated halohydrocarbons containing fluorine (and optionally chlorine and/or bromine) by reaction of a saturated or olefinic compound of the formula $C_nH_mF_pX_q$, wherein each X is independently selected from the group consisting of Cl and Br, n is an integer from 1 to 8, m is an integer from 0 to 16, p is an integer from 1 to 17, and q is an integer from 0 to 15 when the compound contains one double bond, and q is an integer from 1 to 17 when the compound is saturated, provided that $m+p+q$ equals $2n+2$ when the compound is saturated and acyclic, equals $2n$ when the compound either is saturated and cyclic or is acyclic and contains one double bond, and equals $2n-2$ when the compound is cyclic and contains one double bond. Said process comprises the step of reacting a compound of said formula at an elevated temperature with hydrogen in the presence of at least one material selected from iodine and hydrogen iodide, or with hydrogen iodide. A process to produce hydrogen-containing chloromethanes from $CCl_4$ comprising the step of reacting $CCl_4$ at an elevated temperature with hydrogen in the presence of at least one material selected from iodine and hydrogen iodide or with hydrogen iodide is also provided; as is a process to produce $CF_3CCl=CHCF_3$ comprising the step of reacting $CF_3CCl=CClCF_3$ at an elevated temperature with hydrogen in the presence of at least one material selected from iodine and hydrogen iodide or with hydrogen iodide.

It is an object of this invention to provide a process having high conversion to products with added hydrogen.

It is another object of this invention to provide a process having improved selectivity to allow control of the degree of hydrogen addition.

These and other objects of this invention will become evident from the detailed description of the invention which follows.

DETAILED DESCRIPTION OF THE INVENTION

This invention provides a process for producing saturated halohydrocarbons containing fluorine from halogen substituted hydrocarbons which contain fluorine and in addition contain at least one halogen selected from bromine and chlorine and/or contain an olefinic double bond. In some embodiments, the halohydrocarbons produced also contain chlorine and/or bromine. The halogen substituted hydrocarbons which are reacted in accordance with this invention can be saturated acyclic compounds, acyclic compounds with one double bond, saturated cyclic compounds, or cyclic compounds with one double bond. In accordance with this invention a saturated or olefinic compound having the formula $C_nH_mF_pX_q$ is reacted with hydrogen in the presence of at least one material selected from the group consisting of hydrogen iodide and iodine or with hydrogen iodide. In said formula, each X is independently selected from the group consisting of Cl and Br; n is an integer from 1 to 8, m is an integer from 0 to 16, p is an integer from 1 to 17, and q is an integer from 0 to 15 when the compound contains one double bond and is an integer from 1 to 17 when the compound is saturated, provided that $m+p+q$ equals $2n+2$ when the compound is saturated and acyclic, equals $2n$ when the compound either is saturated and cyclic or is acyclic and contains one double bond, and equals $2n-2$ when the compound is cyclic and olefinic.

The compounds of the formula above can contain 1 to 8 carbon atoms, and preferably contain from 1 to 6 carbon atoms. In a preferred embodiment the compounds are represented by the above empirical formula where n is from 1 to 6, m is from 0 to 7, p is from 1 to 13, and q is from 1 to 13. Recent interest in 2-carbon fluorohydrocarbons and chlorofluorohydrocarbons makes embodiments where n is 2 of particular interest. The compounds of the above formula are either commercially available or can be prepared by known methods or by conventional adaptation of known methods.

Hydrogen iodide for the reaction may be provided by several methods. For example, the reaction may be run with stoichiometric HI. Alternatively the reaction may be run with catalytic amounts of HI in the presence of hydrogen. The reaction may also be run with hydrogen using catalytic amounts of iodine. This latter method is preferred for batch reactions and for ease of handling. Without limiting the invention to a particular theory of operation, it is believed that although both molecular and atomic iodine may be present during the reaction, it is the presence of hydrogen iodide during the reaction which provides hydrogen for reducing the halogen substituted hydrocarbon in accordance with this invention.

The use of iodine (either as elemental iodine or as HI) in accordance with this invention allows a high degree of control of the reaction products. Accordingly, a key feature of this invention is that through process control, such as variation of $H_2$/organic ratios, residence time, pressure and temperature, a desired hydrogen containing halocarbon may be obtained as a major product with high selectivity and minimal formation of unwanted byproducts. The reaction may be accomplished in the absence of supported metal catalysts. Indeed the catalyst of this invention typically consists essentially of iodine and/or hydrogen iodide.

The products of the reactions involving compounds of the above formula are saturated and contain both fluorine and hydrogen. In many useful embodiments the reaction is controlled to produce as the major product of the reaction a halohydrocarbon containing the same number of fluorine atoms per molecule as the starting material. For example, the compound $CF_3CHClF$ may be reacted in accordance with this invention to provide as the major product of the reaction (i.e., over 50 mole % of the conversion product) $CF_3CH_2F$. In many useful embodiments using olefinic starting materials, the reaction may be controlled such that there is no removal of halogen from the vinylic position of the olefin and the major product of the reaction is a halohydrocarbon containing the same number of halogens as the starting material. Indeed when using olefinic starting materials, selectivities of about 95% or more are achievable in many useful embodiments without loss of halogen For example, the compound $CF_3C(CF_3)=CFCF_2CF_3$ may be reacted in accordance with this invention to provide as the major product of the reaction $CF_3CH(CF_3)CHFCF_2CF_3$ in high purity.

Chlorine or bromine may also be present in the major products in some embodiments where the formula compound is unsaturated and/or q is greater than one. For example, the compounds $CCl_2FCCl_2F$ and $CClF=CClF$ may each be reacted in accordance with this invention to provide as the major product of the reaction $CHClFCHClF$; $CClF_2CCl_2F$ may be reacted in accordance with this invention to provide as the major product of the reaction $CClF_2CHClF$; and $CF_3CHCl_2$ may be reacted in accordance with this invention to provide as the major product of the reaction $CF_3CH_2Cl$.

The conditions of the reaction can be controlled in accordance with this invention to produce product having fewer chlorine and/or bromine substituents. For example, $CF_3CHClCHClCF_3$ (such as $CF_3CHClCHClCF_3$ produced from $CF_3CCl=CClCF_3$ in accordance with this invention) can be readily reacted to produce $CF_3CHClCH_2CF_3$ as the major product of the reaction; and the process of reacting $CF_3CCl=CClCF_3$ in accordance with this invention can be controlled to produce $CF_3CHClCH_2CF_3$ as the major product of the reaction.

The conditions or the reaction (e.g., temperature, reaction time and/or reactant ratio) may be controlled to produce the desired major product. Furthermore, increasing the amount of iodine and/or hydrogen iodide present is also considered to enhance the reduction rate of the halogenated organic starting material. For example, the compound $CF_3CCl_3$ may be reacted in accordance with this invention to produce either $CF_3CH_2Cl$ or $CF_3CHCl_2$ as the major product of the reaction; and $CF_3CCl=CClCF_3$ may be reacted in accordance with this invention to produce products containing $CF_3CHClCHClCF_3$ and $CF_3CHClCH_2CF_3$ over a broad range of mole ratios. Another novel feature of using hydrogen iodide or using hydrogen in the presence of iodine and/or HI to reduce $CF_3CCl=CClCF_3$ at elevated temperature is that the reaction can also be controlled (e.g., by limiting the relative amount of iodine and/or hydrogen iodide present) to produce $CF_3CCl=CHCF_3$ as the major product.

The preferred products of reacting $C_1$ compounds (i.e., compounds where n is 1) of the formula above in accordance with this invention will contain one to three hydrogen atoms, preferably one or two hydrogen atoms, and most preferably only one hydrogen atom. Accordingly, the reaction is preferably controlled (e.g., by limiting the hydrogen present, the reaction time and/or the temperature) to prevent production of methane as the major product. The products of reacting $C_2$ compounds in accordance with this invention will preferably contain from one to three hydrogen atoms, most preferably one to two. Preferably, the $C_3$ products will contain one to five hydrogen atoms with those containing one to four being most preferred. In a similar manner the $C_4$ to $C_8$ halocarbon products will contain one or more hydrogen atoms.

The reaction is performed at an elevated temperature. The reaction temperature for halohydrocarbons containing fluorine should generally be from about 100° C. to 500° C. A preferred range is 200° C. to 400° C.

In accordance with this invention it has also been found that $CCl_4$ can be reacted with hydrogen in the presence of at least one material selected from the group consisting of iodine and hydrogen iodide or with hydrogen iodide. The product(s) of the $CCl_4$ reaction do not contain fluorine and have the formula $CCl_yH_{4-y}$ where y is an integer from 2 to 3. The reaction of $CCl_4$ is performed at an elevated temperature. The reaction temperature for $CCl_4$ should generally be within the range of from about 150° C. to 400° C. A preferred range is 200° C. to 300° C.

The amount of hydrogen provided for contact with the compound (either by addition of HI or by feed of H₂ gas) should be at a minimum, at least one molecule of hydrogen for each atom of halogen (i.e., chlorine and/or bromine) to be removed from the compound plus one molecule of hydrogen for each olefinic bond to be saturated, and is preferably 10 times said minimum, or less. When hydrogen gas is used, the hydrogen can be fed either in the pure state or diluted with an inert gas, (e.g. nitrogen, helium, or argon).

The reaction may be run at a pressure of from about 50 psi to 5000 psi, with 500 psi to 1500 psi being preferred.

The products of the reaction can be separated and purified by conventional means such as distillation. The products can be used as solvents, blowing agents, refrigerants and propellants.

Practice of the invention will become further apparent from the following non-limiting examples.

EXAMPLES

Example 1

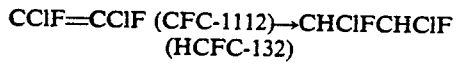
(HCFC-132)

CClF=CClF (CFC-1112, 2 g) was sealed in a 10 mL pressure vessel. The vessel was cooled to −78° C., evacuated, and filled with anhydrous hydrogen iodide (5 g). The vessel was then heated to 200° C. for 1 h, 220° C. for 1h and finally 230° C. for 15 h. It was then cooled to 0° C. and the gases vented. On opening, approx. 0.5 mL of a purple liquid and a small amount of solid iodine were obtained. GC/IR analysis of the liquid showed 90% HCFC-132, 6% acetic acid, and 1% CH₂ClCHF₂ (HCFC-142). Later runs showed no acetic acid formation. It was probably formed from contaminating acetone via a haloform reaction.

Example 2

CClF=CClF (CFC-1112)→CHClFCHClF (HCFC-132)

Iodine (23 g) was sealed in a 400 mL shaker tube. The tube was evacuated and charged with CFC-1112 (50 g) and 1700 psi of hydrogen. The tube was then heated to 240° C. for 1 h and 260° C. for 15 h, followed by cooling to to 0° C. and venting the gases. The liquid in the tube was washed with water and then with a saturated thiosulfate solution. The organic layer was then separated and bulb to bulb distilled to remove non-volatile impurities. This gave a clear liquid (14.9 g) which was analyzed by GC/IR and found to contain 96% HCFC-132, 0.5% CClF₂CH₂Cl (HCFC-132b), 2.5% HCFC-142 and 0.9% CH₂FCHClF (HCFC 142a).

Example 3

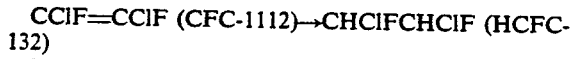

CFC-112 (3 g) and iodine (0.95 g) were sealed in a 10 mL pressure tube. The tube was cooled to −78° C., evacuated, and then charged with 2000 psi of hydrogen at room temperature. The tube was heated to 240° C. for 1 h and 260° C. for 15 h. The tube was then cooled to room temperature, vented, and opened. The liquid inside was removed from the iodine, and washed with water, yielding a light purple liquid (120 mg). Analysis by GC/IR showed 55% HCFC-132, 31% CCl₂FCHClF (HCFC-122a), 5.8% HCFC 132b, 3.3% CFC 112, 2.5% CClF₂CHCl₂ (HCFC-122), 2% HCFC-142a, and 0.4% CCl₂FCH₂F (HCFC-132c).

Example 4

Perfluoro-2-methylpent-2-ene (3 g) and iodine (1.25 g) were sealed in a 10 mL pressure tube. The tube was cooled to −78° C., evacuated, and charged with 1500 psi of hydrogen at room temperature. The tube was then heated at 240° C. for 1 h, and 260° C. for 15 h. The tube was cooled, vented, and opened. The liquid was washed with water, giving 2-trifluoromethyl-1,1,1,3,4,4,5,5,5-octafluoropentane (1.38 g) which was 99.5% pure by GC analysis. GC/IR 3000 cm⁻¹, w (C-H); 1288 cm⁻¹, vs (C-F); 1228 cm⁻¹, vs (C-F); 691 cm⁻¹, m. $^{19}$FNMR −62 ppm, c, 3F; −67.5 ppm, c, 3F; −83.9 ppm, t, 3F; −122-133 ppm, AB, 2F; −212.2 ppm, c, 1F. $^1$HNMR 5.27 ppm, dd, 1H; 3.55 ppm, c, 1H.

Example 5

CF₃CCl₃ (CFC-113a)→CF₃CHCl₂ (HCFC-123)+CF₃CH₂Cl (HCFC-133a)+CF₃CH₃ (HFC-143a)

CFC 113a (3 g) and iodine (1.5 g) were sealed in a 10 mL pressure tube. The tube was cooled to −78° C., evacuated, and then charged with 2000 psi of hydrogen at room temperature. The tube was heated to 240° C. for 1 h and 260° C. for 15 h. The tube was then cooled to −78° C., vented, to remove excess hydrogen, and resealed. The tube was then warmed to room temperature and the gas was analyzed by GC/IR. Analysis showed: 12.9% HCFC 123, 74.7% HCFC 133a, and 10.0% HFC 143a. Upon opening the tube no liquid products were obtained.

Example 6

CF₃CHCl₂ (HCFC-123)→CF₃CH₂Cl (HCFC-133a)+CF₃CH₃ (HFC-143a)

HCFC-123 (3 g) and iodine (1.5 g) were sealed in a 10 mL pressure tube. The tube was cooled to −78° C., evacuated, and then charged with 2000 psi of hydrogen at room temperature. The tube was heated to 240° C. for 1 h and 260° C. for 15 h. The tube was then cooled to −78° C., vented, to remove excess hydrogen, and resealed. The tube was then warmed to room temperature and the gas was analyzed by GC/IR. Analysis showed: 24.8% HCFC-123, 46.0% HCFC-133a, and 19.9% HFC-143a.

Example 7

CClF₂CCl₂F (CFC-113)→CClF₂CHClF (HCFC-123a)+CClF₂CH₂F (HCFC-133b)

CFC-113 (3 g) and iodine (1.5 g) were sealed in a 10 mL pressure tube. The tube was cooled to −78° C., evacuated and charged with 1500 psi of hydrogen at room temperature. The tube was then heated to 240° C. for 1 h, and 260° C. for 15 h. It was then cooled to 0° C., vented and opened, yielding approx 70 mg of a purple liquid which was analyzed by GC/IR. Analysis showed 30.1% CFC-113, 63.5% HCFC-123a, and 2.9% HCFC-133b.

Example 8

Carbon tetrachloride (3 g) and iodine (1.5 g) were sealed in a 10 mL pressure tube. The tube was cooled to −78° C., evacuated and charged with 1500 psi of hydrogen at room temperature. The tube was then heated to the temperature indicated in the table for 15 h. It was then cooled to 0° C., vented and opened. The liquid sample was then analyzed by GC/IR.

| Temp | % CCl$_4$ | % CHCl$_3$ | % CH$_2$Cl$_2$ |
| --- | --- | --- | --- |
| 200° C. | 83.1 | 15.0 | 1.9 |
| 225° C. | 70.5 | 29.3 | 0.2 |
| 260° C. | 41.7 | 55.5 | 0.7 |
| 300° C. | 2.9 | 65.8 | 31.1 |

Example 9

CF$_3$CHClF (HCFC-124)→CF$_3$CH$_2$F (HFC-134a)

Iodine (1 g) was sealed in a 10 mL pressure tube. The tube was cooled to −78° C., evacuated and charged with 3 g of HCFC-124. The tube was then charged with 2000 psi of hydrogen at room temperature. It was then heated to the temperatures shown in the table for the times indicated. The tube was then cooled to −78° C., excess hydrogen vented, warmed to room temperature, and the gas was analyzed by GC/IR.

| Temp | % HCFC-124 | % HFC-134a | % HFC-143a |
| --- | --- | --- | --- |
| 240° C./1 h, 260° C./15 h | 100% | 0% | 0% |
| 290° C./1 h, 300° C./15 h | 98% | 1% | 0% |
| 340° C./1 h, 350° C./15 h | 64.0% | 32.3% | 0.7% |

Example 10

CClF$_2$CCl$_2$F (CFC-113)→CClF$_2$CHClF (HCFC-123a)+CClF$_2$CH$_2$F (HCFC-133b)

Iodine (1 g) was sealed in a 10 mL pressure tube. The tube was cooled to −78° C., evacuated and charged with 3 g of CFC-113. The tube was then charged with 1500 psi of hydrogen at room temperature. It was then heated to 300° C. for 15 h. The tube was then cooled to −b 78° C., vented of excess hydrogen, warmed to room temperature, and the gas was analyzed by GC/IR showing 1.3% CFC-113, 79.6% HCFC-123a, 4.9% HCFC-133b, 0.9% HFC-143a, 0.8% CHF$_2$CH$_2$F (HFC-143), and 8.4% ethane. When the tube was opened, an analysis of the liquid showed 2.7% CFC-113, 95.3% HCFC-123a, and 0.9% HCFC-133b.

Example 11

CBrF$_3$→CHF$_3$ (HFC-23)+CH$_4$

Iodine (1.5 g), was sealed in a 10 mL pressure tube. The tube was cooled to −78° C., evacuated and charged with 3 g of CBrF$_3$. The tube was then charged with 2000 psi of hydrogen at room temperature. It was then heated to 260° C. for 15 h. The tube was then cooled to −78° C., vented of excess hydrogen, warmed to room temperature, and the gas was analyzed by GC/IR, showing 79.8% CBrF3, 1.4% HFC-23, and 17.3% methane.

Example 12

CF$_3$CCl$_2$F (CFC-113a)→CF$_3$CHCl$_2$ (HCFC-123) 30 CF$_3$CH$_2$Cl (HCFC-133a)

CFC 113a (3 g) and iodine (1 g) were sealed in a 10 mL pressure tube. The tube was cooled to −78° C., evacuated, and charged with 1500 psi of hydrogen at room temperature. It was then heated to the temperature shown in the table for the time indicated. The tube was then cooled to −78° C., vented of excess hydrogen, warmed to room temperature, and the gas was analyzed by GC/IR.

| Heat cycle | % 113a | % 123 | % 133a | % 143a |
| --- | --- | --- | --- | --- |
| 220° C./15 h | 40.9 | 53.4 | 2.5 | 0.0 |
| 225° C./15 h | 0.7 | 84.9 | 9.0 | 1.5 |
| 250° C./5 h | 0.0 | 74.6 | 14.0 | 3.8 |
| 250° C./10 h | 0.0 | 56.7 | 29.7 | 13.9 |

EXAMPLE 13

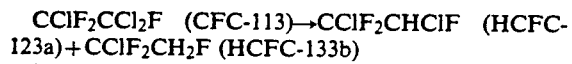

CF$_3$CHClCH$_2$CF$_3$ + CF$_3$CHClCHClCF$_3$ 2,3-Dichlorohexafluorobut-2-ene (100 g) and iodine (55 g) were added to a 400 mL shaker tube. The tube was sealed, cooled, evacuated, and charged with 1500 psi of hydrogen at room temperature. The tube was then heated to 230° C. for 1 hour, 250° C. for 2 hours, and 260° C. for 15 hours. The tube was then cooled to room temperature, vented, and opened. The purple liquid was washed with water and then analyzed by GC/IR. Analysis of the washed liquid showed that it contained about 84% 2-chloro-1,1,1,4,4,4-hexafluorobutane, about 13% 2,3-dichloro-1,1,1,4,4,4-hexafluorobutane and about 1% 1,1,1,4,4,4-hexafluorobutane. The liquid was distilled on a concentric tube column yielding 35 g (41% isolated yield) of 2-chloro-1,1,1,4,4,4-hexafluorobutane (HCFC-346mdf) as a clear liquid with a b.p. of 50.9–51.4° C. $^1$H NMR (CHCl$_3$ as internal standard): 4.4 ppm, complex, 1H; 2.9 ppm, complex, 1H; 2.7 ppm, complex, 1H. $^{19}$F NMR (CCl$_3$F) as internal standard): 64.7 ppm, t, 1F; −76 ppm, d, 1F. GC/IR showed an identical spectrum to an authentic sample.

EXAMPLE 14

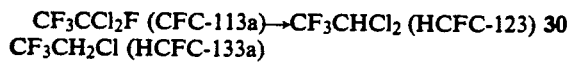

CF$_3$CHClCH$_2$CF$_3$ + CF$_3$CHClCHClCF$_3$ 2,3-Dichlorohexafluorobut-2-ene (300 g) and iodine (150 g) were charged into a 1 liter stirred autoclave. The autoclave was sealed, cooled and evacuated. It was then charged with hydrogen to 500 psi at room temperature. The autoclave was heated to 260° C. and the hydrogen pressure was increased to 1500 psi. The temperature was held at 260° C. with periodic additions of hydrogen to maintain a pressure of 1500 psi. After 15 hours no more hydrogen was being consumed by the reaction. The temperature was held for an additional six hours and then the clave was cooled and the gases were vented. The liquid was washed with water, saturated sodium thiosulfate solution, and then analyzed by GC/IR. Analysis showed that it contained 0.5% 1,1,1,4,4,4-hexafluorobutane, 85% 2-chloro-1,1,1,4,4,4-hexafluorobutane, and 13.5% of 2,3-dichloro- 1,1,1,4,4,4-hexafluorobutane as two isomers. Distillation on a concentric tube column gave 78 g of 2-chloro-1,1,1,4,4,4-hexafluorobutane, and 25 g of 2,3-dichloro-1,1,1,4,4,4-hexafluorobutane as two isomers.

EXAMPLE 15

$$CF_3CHClCHClCF_3 \longrightarrow CF_3CHClCH_2CF_3$$

A mixture (3 g) containing 27.7% 2-chloro-1,1,1,4,4,4-hexafluorobutane, and 71.7% of 2,3-dichloro-1,1,1,4,4,4-hexafluorobutane was added to a 10 mL pressure tube along with iodine (1 g). The tube was sealed, cooled and evacuated. It was then warmed to room temperature and charged with 1500 psi of hydrogen. The tube was then heated to 260° C. for 12 hours, cooled, vented and opened. The liquid was then added to water, washed with sodium thiosulfate, and dried with magnesium sulfate. GC/IR analysis showed that it contained 7.5% 1,1,1,4,4,4-hexafluorobutane, 2.1% 1,1,1,4,4,4-hexafluoro-2-butene, 33.6% 2-chloro-1,1,1,4,4,4-hexafluorobutane, and 55.8% 2,3-dichloro-1,1,1,4,4,4-hexafluorobutane.

EXAMPLE 16

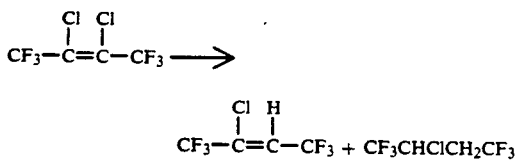

2,3-Dichlorohexafluorobut-2-ene (3 mL; about 4.8 g) and iodine (0.5 g) were added to a 10 mL shaker tube. The tube was sealed, cooled, evacuated, and charged with 1500 psi of hydrogen at room temperature. The tube was then heated to 210° C. for 1 hour, 230° C. for 1 hour, and 250° C. for 12 hours. The tube was then cooled to room temperature, vented and opened. The purple liquid was added to water, and the layers were separated. The lower layer was then shaken with several mL of saturated sodium thiosulfate solution. The organic layer was separated and analyzed by GC/IR. Comparison with authentic samples showed 12% 2-chloro-1,1,1,4,4,4-hexafluorobut-2-ene (cis and trans isomers), 9% 2-chloro-1,1,1,4,4,4-hexafluorobutane, and 77% starting material.

Particular embodiments of the invention are included in the Examples. Other embodiments will become apparent to those skilled in the art from a consideration of the specification or practice of the invention. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the claims.

I claim:

1. A process for producing saturated halohydrocarbons containing fluorine comprising the step of: reacting a saturated compound of the formula $C_nH_mF_pX_q$ wherein each X is independently selected from Cl and Br, n is an integer from 1 to 8, m is an integer from 0 to 16, p is an integer from 1 to 17 and q is an integer from 1 to 17, and wherein m+p+q equals 2n+2 when the compound is acylic and equals 2n when the compound is cyclic, at a temperature from about 100° C. to 500° C. (i) with hydrogen in the presence of at least one material selected from the group consisting of iodine and hydrogen iodide or (ii) with hydrogen iodide, to produce a saturated product containing fluorine and hydrogen wherein at least one X has been removed.

2. The process of claim 1 wherein the reaction temperature is from 200° C. to 400° C.

3. The process of claim 1 wherein the reaction is run at a pressure at from about 50 psi to 5000 psi.

4. The process of claim 1 wherein the said compound is reacted with hydrogen in the presence of hydrogen iodide.

5. The process of claim 1 wherein said compound is reacted with HI.

6. The process of claim 1 wherein said compound is reacted with hydrogen in the presence of iodine.

7. The process of claim 1 wherein n is from 1 to 6, m is from 0 to 7, p is from 1 to 13, and q is from 1 to 13.

8. The process of claim 1 wherein n is 2.

9. The process of claim 1 wherein the compound is $CCl_2FCCl_2F$ and the major product of the reaction is $CHClFCHClF$.

10. The process of claim 1 wherein the compound is $CF_3CCl_3$ and the major product of the reaction is $CF_3CH_2Cl$.

11. The process of claim 1 wherein the compound is $CF_3CHCl_2$ and the major product of the reaction is $CF_3CH_2Cl$.

12. The process of claim 1 wherein the compound is $CClF_2CCl_2F$ and the major product of the reaction is $CClF_2CHClF$.

13. The process of claim 1 wherein the compound is $CF_3CHClF$ and the major product of the reaction is $CF_3CH_2F$.

14. The process of claim 1 wherein the compound is $CF_3CCl_3$ and the major product of the reaction is $CF_3CHCl_2$.

15. The process of claim 1 wherein the compound is $CF_3CHClCHClCF_3$ and the major product of the reaction is $CF_3CHClCH_2CF_3$.

16. The process of claim 1 wherein q is greater than one, and the major product of the reaction contains chlorine or bromine.

17. A process for producing a compound of the formula $CCl_yH_{4-y}$ where y is an integer from 2 to 3 comprising the step of reacting $CCl_4$ at a temperature from about 150° C. to 400° C. (i) with hydrogen in the presence of at least one material selected from the group consisting of iodine and hydrogen iodide or (ii) with hydrogen iodide.

18. The process of claim 7 wherein the reaction temperature is from 200° C. to 300° C.

19. A process for producing $Cf_3CCl=CHCF_3$ comprising the step of reacting $CF_3CCL=CCLCF_3$ at a temperature from about 100° C. to 500° C. (i) with hydrogen in the presence of at least one material selected from the group consisting of iodine and hydrogen iodine or (ii) with hydrogen iodide.

* * * * *